US012646609B2

(12) United States Patent　　　　(10) Patent No.:　US 12,646,609 B2
Vardi et al.　　　　　　　　　　　(45) Date of Patent:　　Jun. 2, 2026

(54) EDGE DETECTION BRUSH

(71) Applicant: Novocure GmbH, Root (CH)

(72) Inventors: Mor Vardi, Haifa (IL); Gil Zigelman, Haifa (IL); Samer Ghantous, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 18/758,442

(22) Filed: Jun. 28, 2024

(65) Prior Publication Data

US 2025/0006347 A1　　　Jan. 2, 2025

Related U.S. Application Data

(60) Provisional application No. 63/609,246, filed on Dec. 12, 2023, provisional application No. 63/524,387, (Continued)

(51) Int. Cl.
G16H 30/40　　　(2018.01)
G06T 7/13　　　(2017.01)
(Continued)

(52) U.S. Cl.
CPC .............. G16H 30/40 (2018.01); G06T 7/13 (2017.01); G06T 7/136 (2017.01); G06T 7/62 (2017.01)

(58) Field of Classification Search
CPC .. G06T 7/12; G06T 7/13; G06T 7/136; G06T 2207/20104; G06T 2207/20116;
(Continued)

(56) References Cited

U.S. PATENT DOCUMENTS

| | | | |
|---|---|---|---|
| 6,553,152 B1 | 4/2003 | Miller et al. | |
| 7,376,252 B2 * | 5/2008 | Gritzky ................. | A61B 8/461 |
| | | | 382/199 |

(Continued)

FOREIGN PATENT DOCUMENTS

| | | |
|---|---|---|
| EP | 3 731 179 A1 | 10/2020 |
| JP | 2022-529327 | 6/2022 |

(Continued)

OTHER PUBLICATIONS

M. Joliot and B. M. Mazoyer, "Three-dimensional segmentation and interpolation of magnetic resonance brain images," in IEEE Transactions on Medical Imaging, vol. 12, No. 2, pp. 269-277, Jun. 1993, doi: 10.1109/42.232255.. (Year: 1993).*

(Continued)

*Primary Examiner* — Courtney Joan Nelson
(74) *Attorney, Agent, or Firm* — McCarter & English, LLP; Michael A. Sartori

(57) ABSTRACT

A method for processing a medical image of a subject is provided. The method includes presenting on a display a slice through the medical image of the subject. The medical image includes voxels. The method further includes performing automatic edge detection in the slice of the medical image to obtain a segmented slice. The automatic edge detection is based on a user selected voxel in the slice of the medical image. The automatic edge detection is based on a user controllable edge detection brush. Not all of the voxels selected by the edge detection brush are designated as an edge.

19 Claims, 7 Drawing Sheets

Related U.S. Application Data filed on Jun. 30, 2023, provisional application No. 63/524,470, filed on Jun. 30, 2023.

(51) Int. Cl.
    *G06T 7/136*      (2017.01)
    *G06T 7/62*      (2017.01)

(58) Field of Classification Search
    CPC ............ G06T 7/62; G06T 2207/20108; G06T 2207/30004; G06T 2207/30096; G06T 7/174; G06T 7/75; G06T 2200/24; G06T 2207/20132; G06T 7/0012; G06T 7/10; G06V 10/751; G06V 10/26; G06V 10/40; G06V 10/945; G16H 30/40; G16H 50/30; A61B 8/461; A61B 8/463; A61B 8/465; A61B 8/469; A61B 8/5223
    See application file for complete search history.

(56) References Cited

U.S. PATENT DOCUMENTS

| | | | |
|---|---|---|---|
| 7,565,205 B2 | 7/2009 | Palti | |
| 8,019,133 B2 | 9/2011 | Knoplioch et al. | |
| 8,547,402 B2 | 10/2013 | Kreeger et al. | |
| 8,689,127 B1* | 4/2014 | Ding | G06T 7/13 |
| | | | 715/771 |
| 8,819,591 B2 | 8/2014 | Wang et al. | |
| 9,135,400 B2 | 9/2015 | McIntyre et al. | |
| 9,678,620 B2 | 6/2017 | Wiemker et al. | |
| 9,710,730 B2 | 7/2017 | Konukoglu et al. | |
| 9,848,799 B2 | 12/2017 | Govari et al. | |
| 10,096,382 B2 | 10/2018 | Zhu et al. | |
| 10,147,185 B2* | 12/2018 | Riklin Raviv | G16H 50/50 |
| 10,188,851 B2 | 1/2019 | Wenger et al. | |
| 10,203,395 B2 | 2/2019 | Foxall et al. | |
| 10,286,216 B2 | 5/2019 | Stone et al. | |
| 10,740,933 B2 | 8/2020 | Tripathi et al. | |
| 10,966,688 B2 | 4/2021 | Fialkov | |
| 11,020,077 B2 | 6/2021 | Wang et al. | |
| 11,109,773 B2 | 9/2021 | Urman et al. | |
| 11,282,193 B2 | 3/2022 | Harrison et al. | |
| 11,417,071 B1 | 8/2022 | Douglas et al. | |
| 11,423,603 B2 | 8/2022 | Sutton et al. | |
| 11,620,789 B2 | 4/2023 | Hershkovich et al. | |
| 11,625,151 B2 | 4/2023 | Gulaka et al. | |
| 2005/0036668 A1 | 2/2005 | McLennan et al. | |
| 2005/0228250 A1* | 10/2005 | Bitter | A61B 34/20 |
| | | | 600/407 |
| 2006/0177133 A1 | 8/2006 | Kee | |
| 2009/0251465 A1 | 10/2009 | Hassenpflug | |
| 2013/0074005 A1* | 3/2013 | Whitman | G06F 3/0481 |
| | | | 715/799 |
| 2016/0042537 A1 | 2/2016 | Ng et al. | |
| 2018/0160933 A1 | 6/2018 | Urman et al. | |
| 2020/0146586 A1 | 5/2020 | Naveh et al. | |
| 2020/0219261 A1 | 7/2020 | Shamir et al. | |
| 2020/0372705 A1* | 11/2020 | Hershkovich | G06T 17/00 |
| 2021/0038314 A1 | 2/2021 | Wibowo | |
| 2021/0162228 A1 | 6/2021 | Urman et al. | |
| 2021/0187289 A1 | 6/2021 | Munster et al. | |
| 2021/0201572 A1 | 7/2021 | Bomzon | |
| 2021/0299439 A1 | 9/2021 | Shamir et al. | |
| 2021/0327105 A1* | 10/2021 | Morard | G06T 5/73 |
| 2022/0096853 A1 | 3/2022 | Bakalo et al. | |
| 2022/0139531 A1 | 5/2022 | Wang et al. | |
| 2022/0151037 A1 | 5/2022 | Taniguchi et al. | |
| 2022/0245821 A1 | 8/2022 | Ouzounis | |
| 2022/0284585 A1 | 9/2022 | Holtzman Gazit et al. | |
| 2022/0292687 A1 | 9/2022 | Yuzawa | |
| 2022/0414883 A1 | 12/2022 | Shinagawa et al. | |
| 2023/0082049 A1* | 3/2023 | Moreau | G06T 17/205 |
| | | | 345/419 |
| 2023/0143748 A1 | 5/2023 | Butler et al. | |
| 2023/0206548 A1 | 6/2023 | Hershkovich et al. | |

FOREIGN PATENT DOCUMENTS

| | | |
|---|---|---|
| WO | WO-2013/155358 A1 | 10/2013 |
| WO | WO-2020225599 | 11/2020 |
| WO | WO-2021/111186 A1 | 6/2021 |
| WO | WO-2022/185222 A1 | 9/2022 |

OTHER PUBLICATIONS

Bevacqua et al., "A Method for Effective Permittivity and Conductivity Mapping of Biological Scenarios via Segmented Contrast Source Inversion," 2019.

Chowdhury et al., "Concurrent segmentation of the prostate on MRI and CT via linked statistical shape models for radiotherapy planning," Apr. 3, 2012.

Davis et al., "LeGUI: A Fast and Accurate Graphical User Interface for Automated Detection and Anatomical Localization of Intracranial Electrodes," Dec. 9, 2021.

Paiement et al., "Integrated Segmentation and Interpolation of Sparse Data," 2013.

Iredale, et al., "Planning system for the optimization of electric fifield delivery using implanted electrodes for brain tumor control," Sep. 1, 2022.

Cates, et al., "GIST: An Interactive, GPU-Based Level Set Segmentation Tool for 3D Medical Images," Feb. 27, 2004.

Rivest-Henault et al., "Robust inverse-consistent affine CT-MR registration in MRI-assisted and MRI-alone prostate radiation therapy," Apr. 24, 2015.

Timmons et al., "End-to-end workflow for finite element analysis of tumor treating fields in glioblastomas," Oct. 11, 2017.

Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial by Ballo MT et al., Int J Radiat Oncol Biol Phys. 2019;104(5):1106-1113.

Wenger et al., "A Review on Tumor-Treating Fields (TTFIELDS): Clinical Implications Inferred from Computational Modeling," IEEE Reviews in Biomedical Engineering, vol. 11, Feb. 13, 2018, pp. 195-207.

Urman et al., "Investigating the Connection Between Tumor-Treating Fields Distribution in the Brain and Glioblastoma Patient Outcomes. A Simulation-Based Study Utilizing a Novel Model Creating Technique: Computational Homan Modeling at EMBC 2018", pp. 139-154.

\* cited by examiner 200 (104)

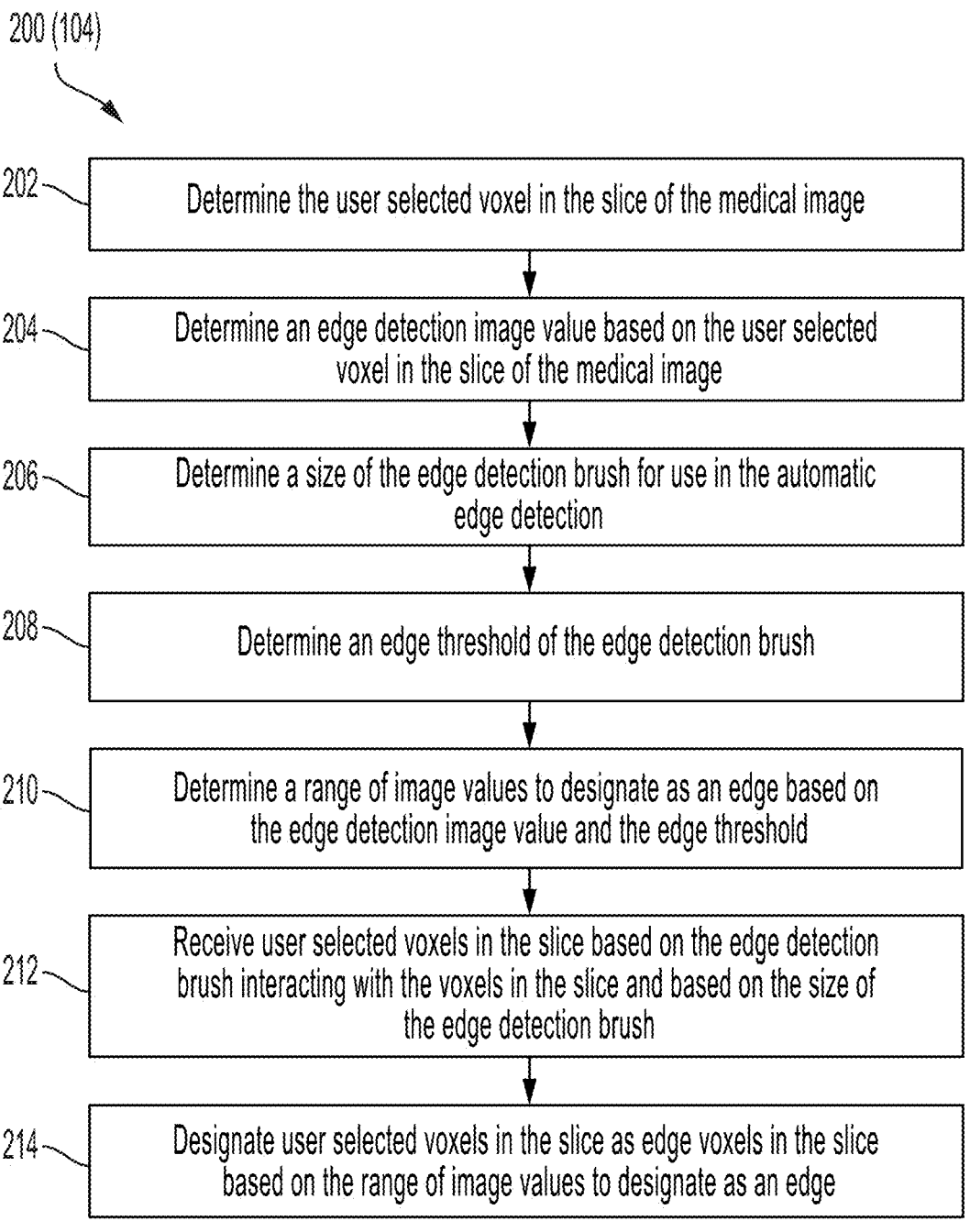

202 — Determine the user selected voxel in the slice of the medical image

204 — Determine an edge detection image value based on the user selected voxel in the slice of the medical image 206 — Determine a size of the edge detection brush for use in the automatic edge detection 208 — Determine an edge threshold of the edge detection brush 210 — Determine a range of image values to designate as an edge based on the edge detection image value and the edge threshold 212 — Receive user selected voxels in the slice based on the edge detection brush interacting with the voxels in the slice and based on the size of the edge detection brush 214 — Designate user selected voxels in the slice as edge voxels in the slice based on the range of image values to designate as an edge

FIG. 2

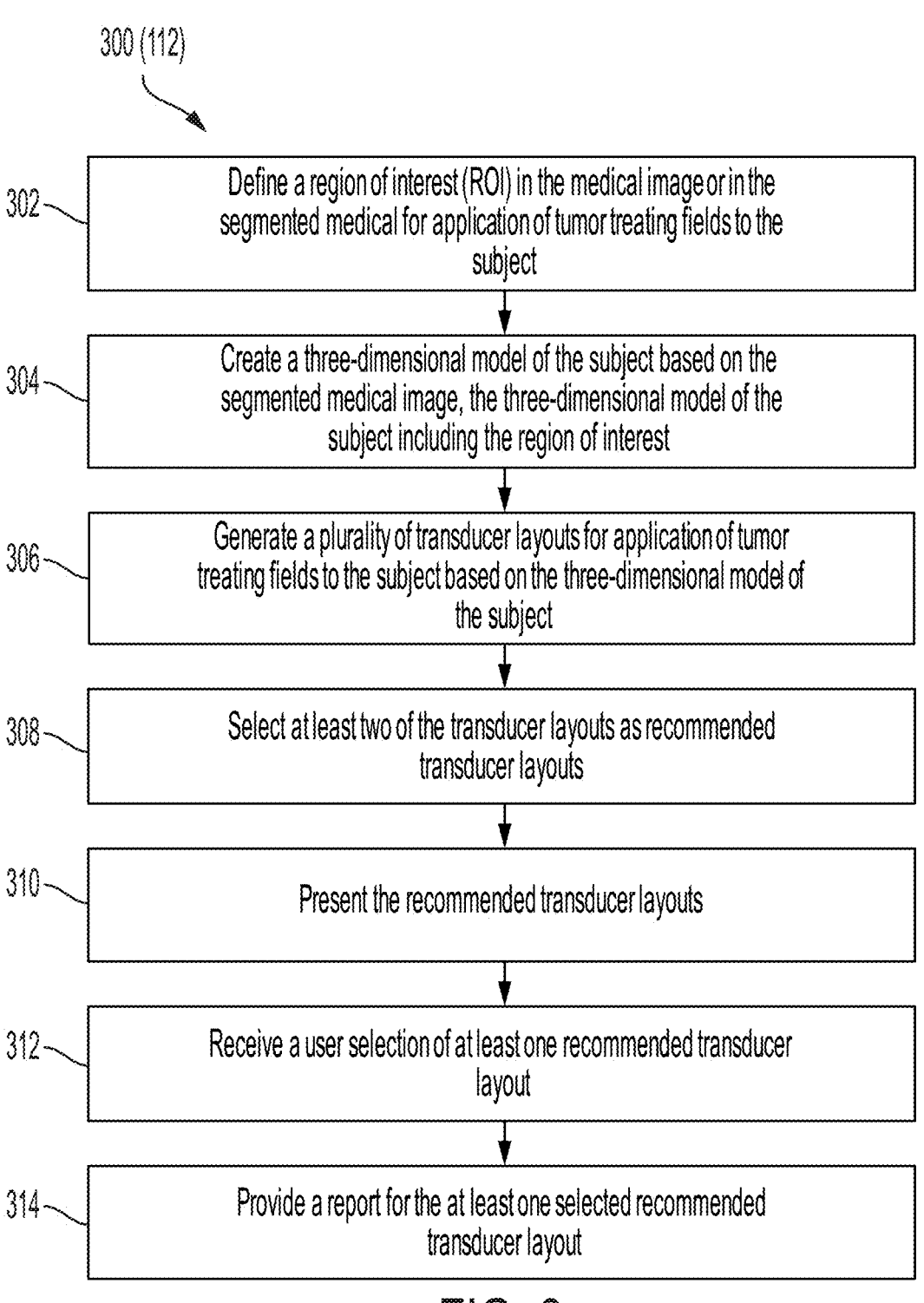

300 (112)

302 — Define a region of interest (ROI) in the medical image or in the segmented medical for application of tumor treating fields to the subject 304 — Create a three-dimensional model of the subject based on the segmented medical image, the three-dimensional model of the subject including the region of interest 306 — Generate a plurality of transducer layouts for application of tumor treating fields to the subject based on the three-dimensional model of the subject 308 — Select at least two of the transducer layouts as recommended transducer layouts 310 — Present the recommended transducer layouts 312 — Receive a user selection of at least one recommended transducer layout 314 — Provide a report for the at least one selected recommended transducer layout

FIG. 3

EDGE DETECTION BRUSH

CROSS-REFERENCE TO RELATED APPLICATIONS

This application claims priority to U.S. Provisional Application No. 63/609,246 filed Dec. 12, 2023, U.S. Provisional Application No. 63/524,470 filed Jun. 30, 2023, and U.S. Provisional Application No. 63/524,387 filed Jun. 30, 2023, the contents of each of which are incorporated by reference herein in their entirety. This application is related to U.S. patent application Ser. No. 18/750,582 filed Jun. 21, 2024 and U.S. patent application Ser. No. 18/750,190 filed Jun. 21, 2024, the contents of each of which are incorporated by reference herein in their entirety.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. In current commercial systems, TTFields are induced non-invasively into a region of interest by electrode assemblies (e.g., arrays of capacitively coupled electrodes, also called electrode arrays, transducer arrays or simply "transducers") placed on the patient's body and applying alternating current (AC) voltages between the transducers. Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

BRIEF DESCRIPTION OF THE DRAWINGS

FIG. 2 is a flowchart depicting an example computer-implemented method for automatic edge detection in a medical image of a subject according to an embodiment.

FIG. 3 is a flowchart depicting an example computer-implemented method for generating transducer layouts for application of tumor treating fields to a subject according to an embodiment.

Various embodiments are described in detail below with reference to the accompanying drawings, wherein like reference numerals represent like elements.

DESCRIPTION OF EMBODIMENTS

Figure 1:
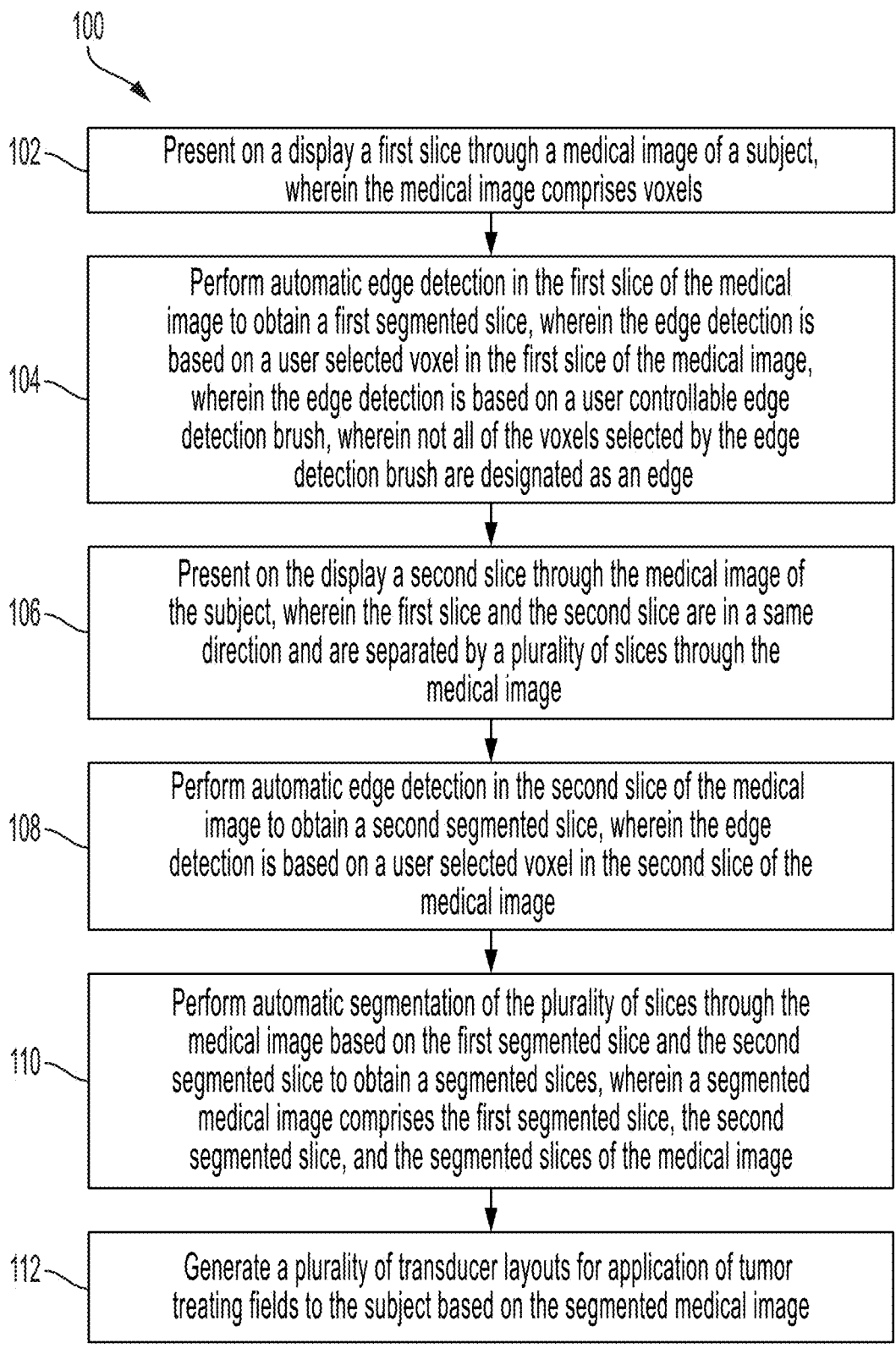
FIG. 1 is a flowchart depicting an example computer-implemented method for processing a medical image of a subject to generate transducer layouts for application of tumor treating fields to the subject according to an embodiment.

When generating transducer layouts for application of tumor treating fields (TTFields) for a subject, medical images of the subject are often used. Examples of such medical images are magnetic resonance imaging (MRI) scans, computed tomography (CT) medical image, positron emission tomography (PET) medical images, and/or the like including combinations and/or multiples thereof. Segmentation is often performed on medical images to divide a medical image into two or more segments with each segment representing a different object of interest. A medical image is often segmented to extract or isolate an object of interest (e.g., abnormal tissue) in the medical image from other structures (e.g., healthy tissue). For example, a medical image can be segmented to isolate a tumor from heathy tissue. Segmentation can be performed manually, semi-automatically, and/or automatically.

As discovered by the inventors, when generating transducer layouts for application of TTFields for a subject, it can be difficult to perform segmentation on medical images, which is a technical problem. For example, separating tissue associated with a tumor or other similar object (e.g., abnormal tissue) from non-tumorous tissue (e.g., healthy tissues) is difficult because of the irregular shape of the tissues, the resolution of the medical images, noise in the medical images, and other similar factors. Further, segmentation is performed on each slice of a medical image. When performed manually, segmentation is a time consuming process because segmentation is performed on each slice of the medical image to isolate abnormal tissues from healthy tissue. As discovered by the inventors, partially and/or fully automating segmentation of medical images would save time and improve segmentation results, thereby improving transducer layouts for application of TTFields.

One or more embodiments described herein provide a technical solution to address this technical problem of preforming segmentation on a medical image for use in generating transducer layouts for application of TTFields for a subject. One or more embodiments described herein provide a computer-implemented method for processing a medical image of a subject to generate transducer layouts for application of TTFields to the subject. One or more embodiments described herein provide a computer-implemented method for automatic edge detection in a medical image of a subject. One or more embodiments described herein provide a computer-implemented method for generating transducer layouts for application of TTFields to a subject. Due to the amount of data and the computational complexities involved, the technical solution cannot be performed by a human mind and, instead, needs to be performed by the computer-based techniques described herein.

In some embodiments, when a medical image is received, a first slice of the medical image can be presented to a user. The user selects a voxel in the first slice of the medical image. The selected voxel is used to automatically detect edges in the first slice using a user controllable edge detection brush. That is, the user defines the edge detection brush and uses the brush to indicate an object of interest (e.g., a tumor) on the slice. Automatic edge detection designates some, but not all, of the voxels selected by the edge detection brush as an edge of the object of interest (e.g., the tumor). This results in a first segmented slice. A second slice of the medical image is then displayed, where one or more intermediate slices exist between the first and second slice. Automatic edge detection is then performed on the second slice of the medical image to generate a second segmented slice. Then, using the first segmented slice and the second segmented slice, automatic segmentation of the intermediate slice(s) is performed to obtain segmented slices. A transducer layout for application of TTFields of the subject is then generated based on the segmented medical image.

One or more embodiments described herein provide a practical application of generating transducer layouts based on medical images for the user. By using the medical images, such as MRI, CT, and/or PET medical images, the subject's tissue conductivity is considered when generating transducer layouts for treating the subject with TTFields. By automating the segmentation process, the medical images can be used more effectively and can be more efficiently reviewed and processed to generate transducer layouts for application of TTFields to the subject. For example, the tools aid in pinpointing the area of the subject to be treated (e.g., where to focus an alternating electric field relative to the subject). These and other technical improvements may be realized using the one or more embodiments described herein.

FIG. 1 is a flowchart depicting an example computer-implemented method 100 for processing a medical image of a subject to generate transducer layouts for application of tumor treating fields to the subject. Certain steps of the method 100 are described as computer-implemented steps. The computer may be, for example, any device comprising one or more processors and memory accessible by the one or more processors, the memory storing instructions that when executed by the one or more processors cause the computer to perform the relevant steps of the method 100. The method 100 may be implemented by any suitable system or apparatus, such as the computer apparatus of FIG. 9. While an order of operations is indicated in FIG. 1 for illustrative purposes, the timing and ordering of such operations may vary where appropriate without negating the purpose and advantages of the examples set forth in detail herein.

With reference to FIG. 1, at step 102, the method 100 includes presenting on a display a first slice through a medical image of the subject. The medical image includes voxels, where a voxel is a three-dimensional representation of a point on the image. As an example, the medical image may be an MRI image, CT image, PET image, and/or the like including combinations and/or multiples thereof. According to one or more embodiments described herein, the medical image includes a torso of the subject, a head of the subject, and/or another suitable body part(s) of the subject.

At step 104, the method 100 includes performing automatic edge detection in the first slice of the medical image to obtain a first segmented slice. For example, a user draws on the medical image using an edge detection brush, and edges are detected from the medical image based on what the user draws. More particularly, the edge detection is based on a user selected voxel (the voxel being selected by the user using the edge detection brush) in the first slice of the medical image, for example. The automatic edge detection is based on the user controllable edge detection brush. It should be appreciated that not all of the voxels selected by the edge detection brush are designated by an edge. For example, a user selects an edge detection brush using an interface of an application for automatic edge detection.

Figure 4:
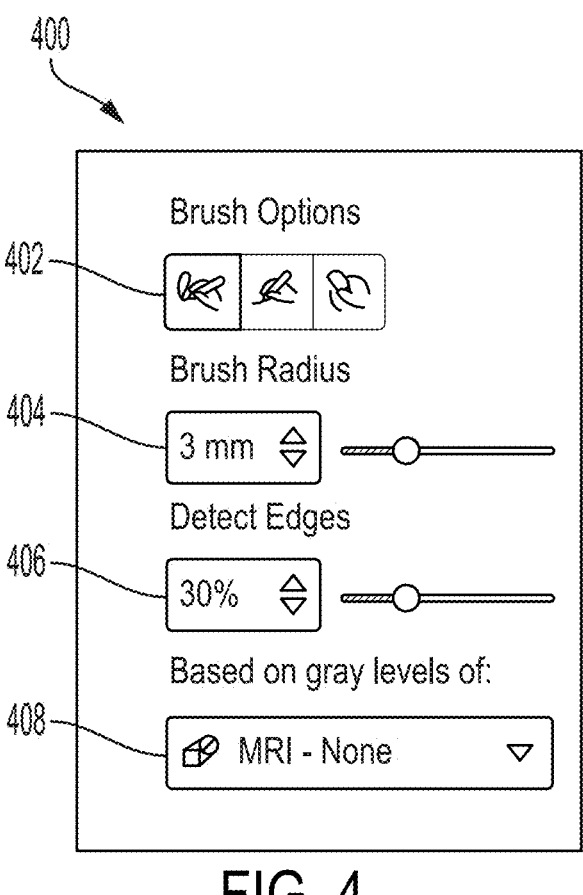
FIG. 4 is an example interface of an application for automatic edge detection according to an embodiment.

FIG. 4 is an example interface 400 of such an application for automatic edge detection. In this example, the interface 400 includes brush option 402, a brush radius option 404, a detect edges option 406, and a gray level selection option 408. The user can select from the options 402, 404, 406, 408, and the user selections are used to perform the automatic edge detection. The brush options 402 include types of brushes, such as a free draw brush, a lasso brush, a polygon brush, and/or the like including combinations and/or multiples thereof. The brush radius option 404 defines a radius of the brush (e.g., 3 millimeters (mm)), and the user can define the brush radius by inputting a value or manipulating arrows and/or a slider, as shown. The detect edges option 406 defines an amount of pixels that are defined as edges as a percentage of the pixels that are selected.

That is, according to one or more embodiments described herein, performing the automated edge detection includes determining a radius of the edge detection brush for use in the automated edge detection and determining an edge threshold of the edge detection brush. Image values of voxels selected by the edge detection brush are designated as an edge based on the edge threshold. For example, when the user draws, using the brush, on the slice, the detect edges option 406 defines what percentage of the pixels selected (e.g., drawn on) by the user are designated as edges.

Consider the following example. If the detect edges option 406 is set to 100%, an exception will occur, so a more reasonable range for the detect edges option 406 is 0% to 90%. A 30% selection for the detect edges option 406 will mean detecting 70% of the 90% (e.g., 63%). The range length is determined by a width of window settings (e.g., contrast and brightness) the user sampled (e.g., the user clicks with the brush and samples a median intensity in the center of the brush and a certain number (e.g., eight) voxels around the center of the brush). As such, a selection of 0% will detect all voxels in the range as edges. A selection of 30% will detect 70% from the 100% (e.g., 70% of the 90%=63%). So, the range is [min, max]=relevant range=width*(1−tolerance*0.9). For example, for a median value of 100 and a tolerance of 70%, a width (e.g., range length) of 1000 yields a relevant range of 1000*(1−(0.7*0.9))=370. Further details of the automatic edge detection are described herein with reference to FIG. 2.

With continued reference to FIG. 1, at step 106, the method 100 includes presenting on the display a second slice through the medical image of the subject. In this example, the first slice and the second slice are in a same direction and are separated by a plurality of slices through the medical image.

At step 108, the method 100 includes performing automatic edge detection in the second slice of the medical image to obtain a second segmented slice, wherein the edge detection is based on a user selected voxel in the second slice of the medical image.

At step 110, the method 100 includes performing automatic segmentation of the plurality of slices between the first slice and the second slice based on the first segmented slice and the second segmented slice to obtain segmented slices, wherein a segmented medical image comprises the first segmented slice, the second segmented slice, and the segmented slices of the medical image. According to one or more embodiments described herein, the plurality of slices are automatically segmented by interpolating between the segmentations in the first segmented slice and the segmentations in the second segmented slice. According to one or more embodiments described herein, a segmented slice includes at least one of a resection cavity or an edema of the subject having an edge detected by the automatic edge detection. A resection cavity may refer to a cavity caused by removal of a tissue, a structure, or an organ. An edema may refer to a swelling caused by fluid retention. As an example, a number of automatically segmented slices between a pair of segmented slices is between 2 and 20. As another example, a number of automatically segmented slices between a pair of segmented slices is between 2 and 5. Other numbers of automatically segmented slices are also possible.

At step 112, the method 100 includes generating a plurality of transducer layouts for application of tumor treating fields to the subject based on the segmented medical image.

According to one or more embodiments described herein, the method 100 can include one or more additional steps. For example, the method 100 can include determining transducer locations for TTFields. Further details of determining transducer locations for TTFields are described herein with reference to FIG. 3.

FIG. 2 is a flowchart depicting an example computer-implemented method 200 for automatic edge detection in a medical image of a subject. According to one or more embodiments described herein, step 104 of FIG. 1 may be implemented using method 200. Certain steps of the method 200 are described as computer-implemented steps. The computer may be, for example, any device comprising one or more processors and memory accessible by the one or more processors, the memory storing instructions that when executed by the one or more processors cause the computer to perform the relevant steps of the method 200. The method 200 may be implemented by any suitable system or apparatus, such as the computer apparatus of FIG. 9. While an order of operations is indicated in FIG. 2 for illustrative purposes, the timing and ordering of such operations may vary where appropriate without negating the purpose and advantages of the examples set forth in detail herein.

With reference to FIG. 1, at step 202, the method 200 includes determining the user selected voxel in the slice of the medical image. The user selected voxel may be in a center of a user selected location in the slice of the medical image.

At step 204, the method 200 includes determining an edge detection image value based on the user selected voxel in the slice of the medical image. According to one or more embodiments described herein, determining the edge detection image value based on the user selected voxel in the slice of the medical image includes: determining a center image value as an image value of the user selected voxel in the slice of the medical image, wherein the user selected voxel is in a center of a user selected location; determining adjacent image values as image values of voxels adjacent to the user selected voxel; calculating an average image value based on the center image value and the adjacent image values; and assigning the edge detection image value as the average image value. According to one or more embodiments described herein, the voxels adjacent to the user selected voxel comprise eight voxels surrounding the user selected voxel. According to one or more embodiments described herein, the voxels adjacent to the user selected voxel may comprise any number of voxels surrounding the user selected voxel, such as two, three, four, five, six, seven, eight, nine, ten or more voxels, such as twenty-four voxels or more voxels. According to one or more embodiments described herein, the voxels adjacent to the user selected voxel may be user defined, pre-defined, or a combination thereof. According to one or more embodiments described herein, determining the edge detection image value based on the user selected voxel in the slice of the medical image includes: determining a center image value as an image value of the user selected voxel in the slice of the medical image, wherein the user selected voxel is in a center of a user selected location; and assigning the edge detection image value as the center image value.

At step 206, the method 200 includes determining a size of the edge detection brush for use in the automatic edge detection. According to one or more embodiments described herein, the size of the edge detection brush may be determined by a shape of the edge detection brush, such as a free draw brush, a lasso brush, a polygon brush, and/or the like including combinations and/or multiples thereof. According to one or more embodiments described herein, the type of edge detection brush may be user defined, pre-defined, or a combination thereof. As an example, in FIG. 4, the brush option 402 provides a default pre-defined edge detection brush and user selectable icons to change the pre-defined edge detection brush. According to one or more embodiments described herein, the size of the edge detection brush is a radius of an edge detection brush, such as a circular edge detection brush. According to one or more embodiments described herein, the size of the edge detection brush may be user defined, pre-defined, or a combination thereof. As an example, in FIG. 4, the brush radius option 404 provides a default pre-defined value (e.g., 3 mm) and user selectable icons and a user adjustable data field to change the pre-defined value of the size of the edge detection brush.

At step 208, the method 200 includes determining an edge threshold of the edge detection brush. According to one or more embodiments described herein, a user section of the edge threshold for the edge detection brush is defined as a percentage and/or an image value. According to one or more embodiments described herein, the edge threshold for the edge detection brush may be user defined, pre-defined, or a combination thereof. As an example, in FIG. 4, the detect edges option 404 provides a default pre-defined value (e.g., 30%) and user selectable icons and a user adjustable data field to change the pre-defined value of the edge threshold of the edge detection brush.

At step 210, the method 200 includes determining a range of image values to designate as an edge based on the edge detection image value and the edge threshold.

According to one or more embodiments described herein, the range of image values to designate as an edge includes a number M of image values in the range, an upper limit UL of the range, and a lower limit LL of the range. The number M of image values is $M=N*(1-P)$, where a range of image values for the medical image has a maximum number N of image values, and where the user selection for the edge threshold is a percentage P. The upper limit UL of the range is $UL=IV+0.5*M$, where image value IV is the edge detection image value. The lower limit LL of the range is $LL=IV-0.5*M$. As an example, for N=1000 and P=0.7, M=300, and for IV=600, UL=750 and LL=450.

According to one or more embodiments described herein, the range of image values to designate as an edge includes a number M of image values in the range, an upper limit UL of the range, and a lower limit LL of the range. The number M of image values is in the range $M=N*(1-(P*RL))$, where range of image values for the medical image has a maximum number N of image values, where the user selection for the edge threshold is a percentage P, and where a range limiter is a percentage RL. The upper limit UL of the range is $UL=IV+0.5*M$, where image value IV is the edge detection image value. The lower limit LL of the range is $LL=IV-0.5*M$. As an example, for N=1000, P=0.7, and RL=0.9, M=370, and for IV=600, UL=785 and LL=415.

According to one or more embodiments described herein, the edge threshold is an image value. An upper limit of the range of image values is a sum of the edge detection image value and the edge threshold, and a lower limit of the range of image values is a difference between the edge detection image value and the edge threshold.

At step 212, the method 200 includes receiving user selected voxels in the slice based on the edge detection brush interacting with the voxels in the slice and based on the size of the edge detection brush.

At step 214, the method 200 includes designating user selected voxels in the slice as edge voxels in the slice based on the range of image values to designate as an edge. According to one or more embodiments described herein, designating user selected voxels in the slice as edge voxels in the slice includes comparing image values of the user selected voxels to the range of image values. According to one or more embodiments described herein, designating user selected voxels in the slice as edge voxels in the slice comprises, for each user selected voxel in the slice includes designating the user selected voxel as an edge if an image value of the user selected voxel is in the range of image values, and designating the user selected voxel as not an edge if an image value of the user selected voxel is not in the range of image values. According to one or more embodiments described herein, an image value of a voxel of the slice includes a whole number indicating an intensity of the voxel. According to one or more embodiments described herein, the image value of a voxel of the slice includes a gray level value.

According to one or more embodiments described herein, the plurality of transducer layouts for application of tumor treating fields to the subject are generated based on the segmented slice through the medical images.

FIG. 3 is a flowchart depicting an example computer-implemented method 300 for generating transducer layouts for application of tumor treating fields to a subject. According to one or more embodiments described herein, step 112 of FIG. 1 may be implemented using method 300. Certain steps of the method 300 are described as computer-implemented steps. The computer may be, for example, any device comprising one or more processors and memory accessible by the one or more processors, the memory storing instructions that when executed by the one or more processors cause the computer to perform the relevant steps of the method 300. The method 300 may be implemented by any suitable system or apparatus, such as the computer apparatus of FIG. 9. While an order of operations is indicated in FIG. 3 for illustrative purposes, the timing and ordering of such operations may vary where appropriate without negating the purpose and advantages of the examples set forth in detail herein.

With reference to FIG. 3, at step 302, the method 300 includes defining a region of interest (ROI) in the medical image or in the segmented medical image for application of tumor treating fields to the subject. The ROI defines where the TTFields are to focus. According to one or more embodiments described herein, volumes can be assigned to the regions of interest, such as by using the approach described in "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial" by Ballo M T et al., Int J Radiat Oncol Biol Phys. 2019; 104 (5): 1106-1113.

At step 304, the method 300 includes creating a three-dimensional model of the subject based on the segmented medical image (such as, the segmented medical image determined from steps 102-110 in FIG. 1), where the three-dimensional model of the subject includes the region of interest. According to one or more embodiments described herein, the region of interest in the medical image is part of the 3D model. According to one or more embodiments described herein, a three-dimensional conductivity map is part of the 3D model. The three-dimensional conductivity map may depict the electrical conductivity of the body tissues. Creating the 3D model may include performing calculations to determine conductivity of tissues of the subject based on an anchor medical image, the medical images, and the tissue types in the medical images. For example, creating the 3D model may include assigning tissue types and associated conductivities to voxels of the 3D model of the subject. According to one or more embodiments described herein, creating the 3D model of the subject may include automatically segmenting normal tissue in the medical images.

At step 306, the method 300 includes generating a plurality of transducer layouts for application of tumor treating fields to the subject based on the three-dimensional model of the subject. The transducer layouts define the location, relative to the subject, for placing transducer arrays. According to one or more embodiments described herein, the plurality of the transducer layouts includes four locations on the subject to place four respective transducer arrays, such as on a head or torso of the subject. According to one or more embodiments described herein, each of the transducer arrays comprises one or more electrode elements. The electrode elements can be any suitable type or material. For example, at least one electrode element can include a ceramic dielectric layer, a polymer film, and/or the like including combinations and/or multiples thereof. Generating the plurality of transducer layouts can be performed after receiving a selection by a user from a user interface to begin the generating. According to one or more embodiments described herein, generating the plurality of transducer layouts at step 306 can be performed using techniques in commonly-owned U.S. Patent Application Publication No. 2021/0201572, entitled "METHODS, SYSTEMS, AND APPARATUSES FOR IMAGE SEGMENTATION," the contents of which are incorporated by reference herein in their entirety.

At step 308, the method 300 includes selecting at least two of the transducer layouts as recommended transducer layouts. According to one or more embodiments described herein, at least one of the recommended transducer layouts has a highest dose of tumor treating fields delivered to the ROI, delivered a tumor progression area, and/or the like including combinations and/or multiples thereof. According to one or more embodiments described herein, at least one of the recommended transducer layouts is a transducer layout that is in a shifted or rotated position compared to a transducer layout having a highest does of tumor treating fields delivered to the ROI. According to one or more embodiments described herein, at least three of the recommended transducer layouts have three highest doses of tumor treating fields delivered to the ROI.

At step 310, the method 300 includes presenting the recommended transducer layouts. For example, the method 300 can include presenting one (or at least two, at least three, or at least four) recommended transducer layouts, although more or fewer transducer layouts can be presented in other examples. According to one or more embodiments described herein, presenting the recommended transducer layouts includes presenting information on the recommended transducer layouts via a user interface. The information can include one or more of the following: doses of tumor treating fields delivered to the ROI for each of the recommended transducer layouts, a medical image slice overlaid with a dose of tumor treating fields for at least one recommended transducer layout, a two-dimensional graph comparing percentage volume of ROI and percentage dose of tumor treating fields for at least one recommended transducer layout, an image of the subject depicting locations of electrode elements for at least one recommended transducer layout, a two-dimensional graph depicting a cumulative dose of tumor treating fields across the ROI for at least one recommended transducer layout, a two-dimensional graph depicting a dose of tumor treating fields across the ROI for at least one recommended transducer layout, a percentage of overlap between electrode elements of two recommended transducer layouts, a percentage of overlap between adhesive portions of two recommended transducer layouts, and/or the like including combinations and/or multiples thereof.

At step 312, the method 300 includes receiving a user selection of at least one recommended transducer layout. According to one or more embodiments described herein, the user can select a primary transducer layout and an alternative transducer layout. To make the selection, the user can accept a primary layout as a first layout then review and evaluate alterative layouts and select an alternative layout as a second layout. For example, the user selects one (e.g., a primary) of the transducer layouts for use for a period of time. The user can select another (e.g., an alternate) of the transducer layouts for use after the period of time for another period of time, for example. According to one or more embodiments described herein, the transducer layouts can be approved by entering a username and password. Having two or more transducer layouts enables a subject to change between or among the transducer layouts, which can improve the subject's comfort, for example.

At step 314, the method 300 includes providing a report for the at least one selected recommended transducer layout. According to one or more embodiments described herein, the report can depict locations of transducer arrays of the selected recommended transducer layout on the subject in a plurality of views. According to one or more embodiments described herein, the report can provide dosages of tumor treating fields. It should be appreciated that different reports can be provided, for example, depending on the anticipated target of the report (e.g., a first report type for the subject, a second report type for inclusion in the subject's medical records). According to an embodiment, comments can be added using a text box on an interface, 3D head renderings can be shown and rotated as desired, and the report can be created using the create report button on the interface. According to one or more embodiments described herein, a report can be edited via an interface. In this example, the user can edit the report using an edit button on the interface, can download or print the report using download/print buttons on the interface, can anonymize the report using anonymize button on the interface, can generate different report types (e.g., full report, patient report, and/or the like including combinations and/or multiples thereof) using the type dropdown on the interface, can review different versions of the report using the version dropdown on the interface, can return to patient management using the patient management button on the interface, and can return to the welcome screen using the return button on the interface.

Figure 5:
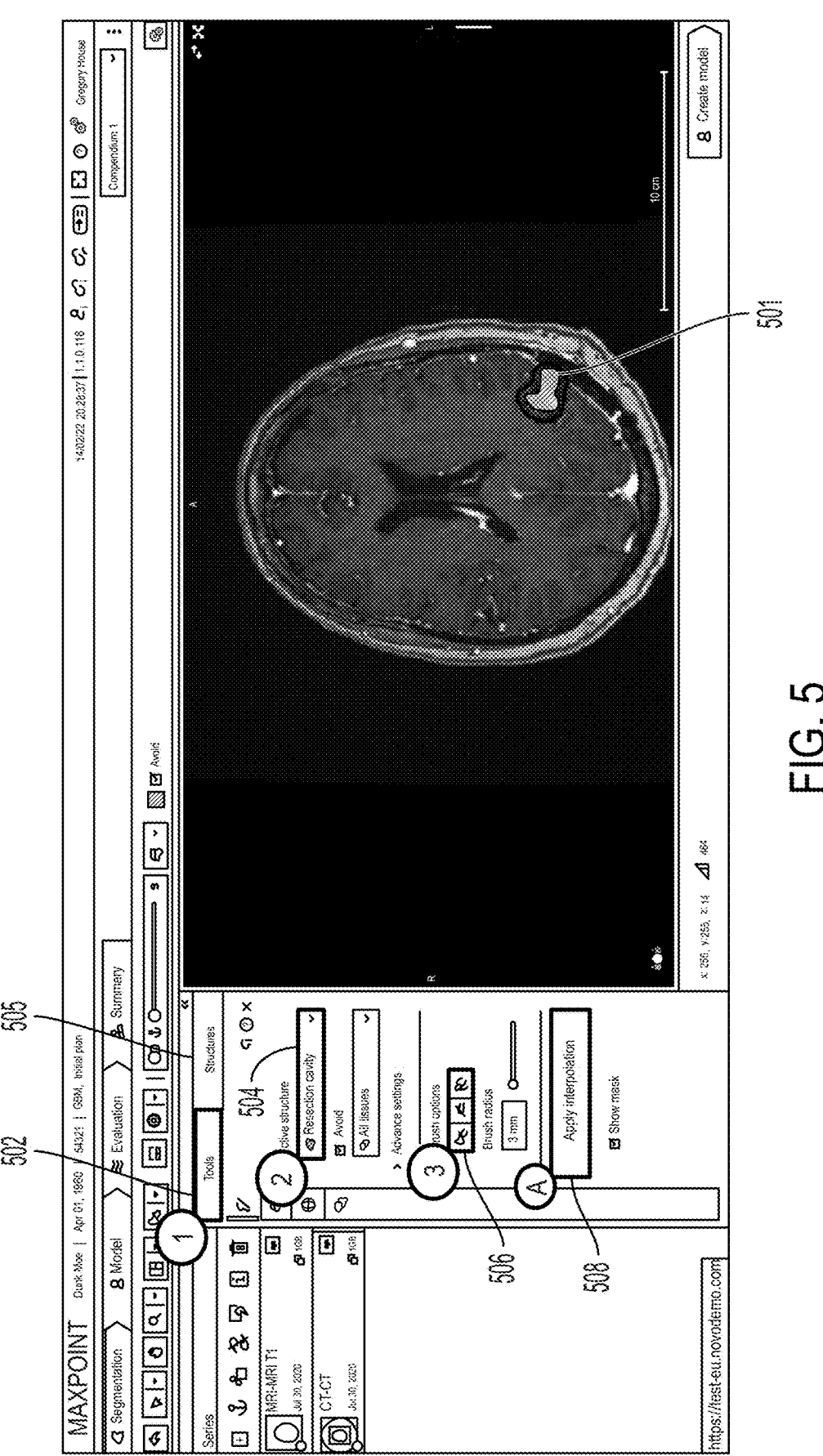
FIG. 5 is an example interface of an application for generating at least one transducer layout for delivering TTFields to a subject according to an embodiment.
Figure 6:
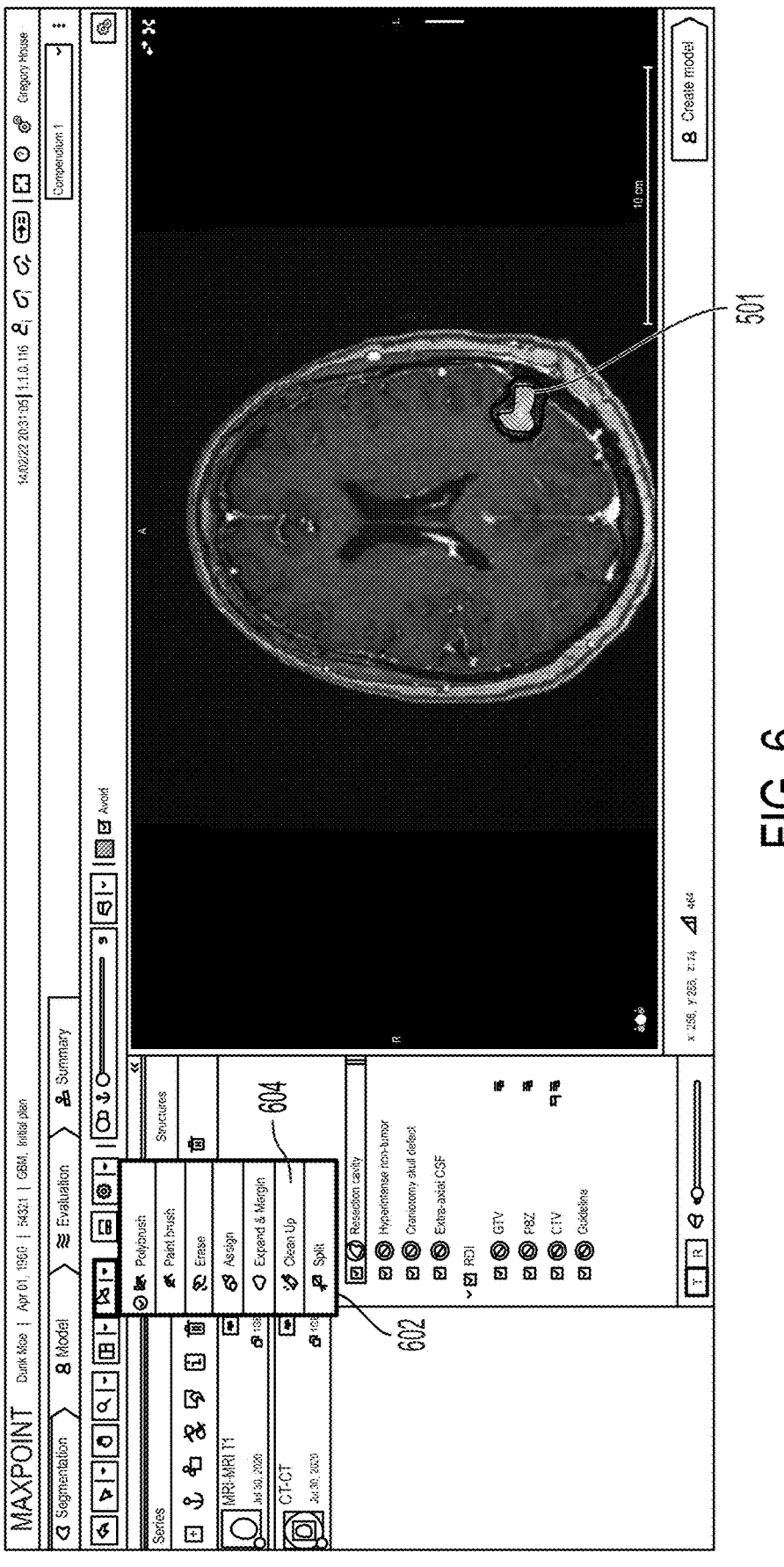
FIG. 6 is an example interface of an application for generating at least one transducer layout for delivering TTFields to a subject according to an embodiment.

FIGS. 5 and 6 are now described. FIG. 5 is an example interface of an application for generating at least one transducer layout for delivering TTFields to a subject. The interface of FIG. 5 supports segmenting an abnormal tissue region 501, for example. As shown in FIG. 5, an abnormal tissue region 501 is indicated. To segment the abnormal tissues, such as the abnormal tissue region 501, a user can select a tools tab 502 to begin contouring structures. Next, the user can select an active structure 504 to contour. It may also be possible to select an active structure from the structures tab 505 in another embodiment. The user can then select a brush 506 (or any other suitable tool) to perform the segmenting. According to one or more embodiments described herein, the brush 506 may be an edge detection brush to perform automatic edge detection as described with respect to FIG. 1. According to one or more embodiments described herein, the brush 506 may be selected using the interface in FIG. 4. According to one or more embodiments described herein, an interpolation tool 508 can be used to expedite the segmenting. For example, a structure can be segmented in a first slice of the medical image (for example, as in steps 102 and 104 of FIG. 1), one or more subsequent slices can be skipped, and then the structure can be segmented again on a next slice following the skipped slices (for example, as in steps 106 and 108 of FIG. 1). The interpolation tool 508 can then be used to apply the segmenting for the skipped slices, where the interpolation segmenting is performed based on the segmenting performed on the slices adjacent to the skipped slices (for example, as in step 110 of FIG. 1). According to one or more embodiments described herein, segmenting the abnormal tissue is based on user input identifying abnormal tissue in the medical images, such as segmenting as described with respect to FIG. 1.

Turning now to FIG. 6, multiple user-selectable options 602 (e.g., user-selectable icons) to manually segment the slice are presented in a drop down menu. Examples of the user-selectable options 602 include, for example, a user-selectable icon to autofill a region (e.g., a polybrush option), a user-selectable icon to select the region without autofill (e.g., a paint brush option), a user-selectable icon to erase a segmentation (e.g., an erase option), a user-selectable icon to assign a tissue type (e.g., an assign option), a user-selectable icon to expand a border of the region (e.g., an expand & margin option), and/or the like including combinations and/or or multiples thereof. According to one or more embodiments described herein, user-selectable options 602 provide a user with a set of tools to select without toggling to the tools tab 502. The tools can be used for segmenting abnormal tissues. For example, a polybrush or paint brush can be used to outline an abnormal tissue region, such as the abnormal tissue region 501. The abnormal tissue can be any undesirable type of tissue, such as a tumor, necrotic tissue, a prior surgical area (e.g., a resection cavity), and/or the like including combinations and/or multiples thereof.

The interface of FIG. 6 can also include a clean-up option 604 which provides for automatically cleaning up a segmented slice (either an automatically segmented slice or a manually segmented slice) to obtain a cleaned up segmented slice through the medical image. For example, the segmented slice is automatically cleaned up by splitting a segmented area of the segmented slice into a first portion and a second portion based on gray scale values. The first portion is identified as normal tissue and the second portion is identified as abnormal tissue. The abnormal tissue can include a tumor, necrotic tissue, a prior surgical area, and/or the like including combinations and/or multiples thereof. As an example, the segmented area is split based on a threshold adjusted by a user-selectable slider of gray scale values. According to one or more embodiments described herein, the segmented slice can be automatically cleaned up by smoothing one or more edges of a segmented area of the segmented slice, removing one or more discontinuous segmented areas outside a larger segmented area of the segmented slice, removing one or more non-segmented areas inside a segmented area of the segmented slice, and/or the like including combinations and/or multiples thereof.

Figures 7, 8, 9:
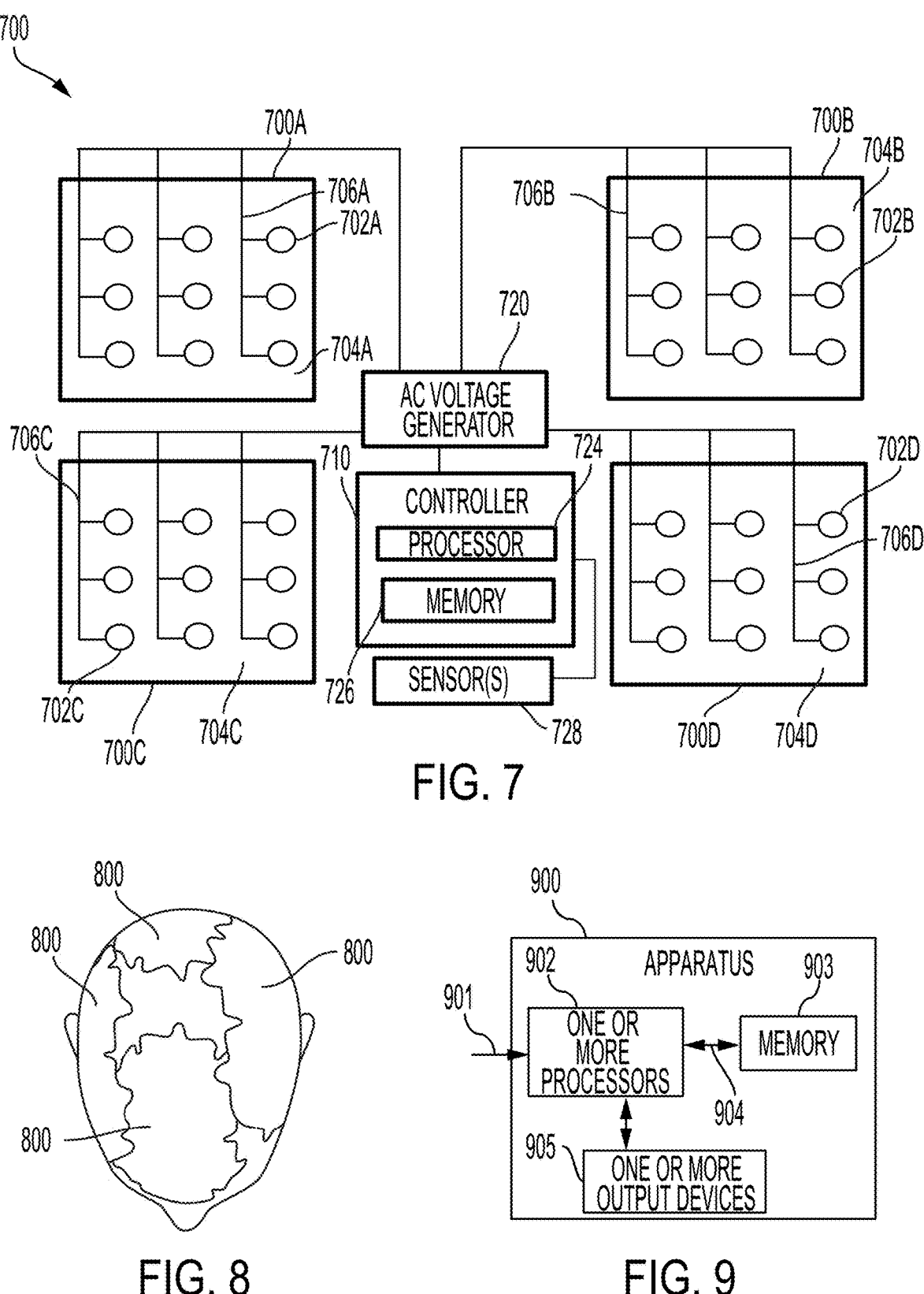
FIG. 7 depicts an example system to apply alternating electric fields to a subject.
FIG. 8 depicts an example placement of transducers on a subject's head.
FIG. 9 depicts an example computer apparatus according to one or more embodiments described herein.

FIG. 7 depicts an example apparatus 700 to apply alternating electric fields (e.g., TTFields) to the subject's body. The system may be used for treating a target region of a subject's body with an alternating electric field. In an example, the target region may be in the subject's brain, and an alternating electric field may be delivered to the subject's body via two pairs of transducer arrays positioned on a head of the subject's body (such as, for example, in FIG. 8, which has four transducers 800). In another example, the target region may be in the subject's torso, and an alternating electric field may be delivered to the subject's body via two pairs of transducer arrays positioned on at least one of a thorax, an abdomen, or one or both thighs of the subject's body. Other transducer array placements on the subject's body may be possible.

The example apparatus 700 depicts an example system having four transducers (or "transducer arrays") 700A-D. Each transducer 700A-D may include substantially flat electrode elements 702A-D positioned on a substrate 704A-D and electrically and physically connected (e.g., through conductive wiring 706A-D). The substrates 704A-D may include, for example, cloth, foam, flexible plastic, and/or conductive medical gel. Two transducers (e.g., 700A and 200D) may be a first pair of transducers configured to apply an alternating electric field to a target region of the subject's body. The other two transducers (e.g., 700B and 700C) may be a second pair of transducers configured to similarly apply an alternating electric field to the target region.

The transducers 700A-D may be coupled to an AC voltage generator 720, and the system may further include a controller 710 communicatively coupled to the AC voltage generator 720. The controller 710 may include a computer having one or more processors 724 and memory 726 accessible by the one or more processors 724. The memory 726 may store instructions that when executed by the one or more processors control the AC voltage generator 720 to induce alternating electric fields between pairs of the transducers 700A-D according to one or more voltage waveforms and/or cause the computer to perform one or more methods disclosed herein. The controller 710 may monitor operations performed by the AC voltage generator 720 (e.g., via the processor(s) 724). One or more sensor(s) 728 may be coupled to the controller 710 for providing measurement values or other information to the controller 710.

In some embodiments, the voltage generation components may supply the transducers 700A-D with an electrical signal having an alternating current waveform at frequencies in a range from about 50 kHz to about 1 MHz and appropriate to deliver TTFields treatment to the subject's body.

The electrode elements 702A-D may be capacitively coupled. In one example, the electrode elements 702A-D are ceramic electrode elements coupled to each other via conductive wiring 706A-D. When viewed in a direction perpendicular to its face, the ceramic electrode elements may be circular shaped or non-circular shaped. In other embodiments, the array of electrode elements are not capacitively coupled, and there is no dielectric material (such as ceramic, or high dielectric polymer layer) associated with the electrode elements.

The structure of the transducers 700A-D may take many forms. The transducers may be affixed to the subject's body or attached to or incorporated in clothing covering the subject's body. The transducer may include suitable materials for attaching the transducer to the subject's body. For example, the suitable materials may include cloth, foam, flexible plastic, and/or a conductive medical gel. The transducer may be conductive or non-conductive.

The transducer may include any desired number of electrode elements (e.g., one or more electrode elements). For example, the transducer may include one, two, three, four, five, six, seven, eight, nine, ten, or more electrode elements (e.g., twenty electrode elements). Various shapes, sizes, and materials may be used for the electrode elements. Any constructions for implementing the transducer (or electric field generating device) for use with embodiments of the invention may be used as long as they are capable of (a) delivering TTFields to the subject's body and (b) being positioned at the locations specified herein. The transducer may be conductive or non-conductive. In some embodiments, an AC signal may be capacitively coupled into the subject's body. In some embodiments, at least one electrode element of the first, the second, the third, or the fourth transducer may include at least one ceramic disk that is adapted to generate an alternating electric field. In some embodiments, at least one electrode element of the first, the second, the third, or the fourth transducer may include a polymer film that is adapted to generate an alternating electric field.

FIG. 9 depicts an example computer apparatus 900 (also referred to as "apparatus 900") for use with the embodiments herein. As an example, the apparatus 900 may be a computer to implement certain inventive techniques disclosed herein, such as processing a medical image of a subject to generate transducer layouts for application of TTFields to the subject. As an example, method 300 of FIG. 3 may be performed by a computer, such as the apparatus 900. As an example, method 100 of FIG. 1 may be performed by a computer, such as the apparatus 900, which may the same computer or a different computer than the computer used to perform the method 200 of FIG. 2 and/or the method 300 of FIG. 3. As an example, steps 102 to 112 of FIG. 1, steps 202 to 214 of FIG. 2, and/or steps 302 to 314 of FIG. 3 may be performed by a computer, such as the apparatus 900. In some embodiments, controller 710 of FIG. 7 may be implemented with the apparatus 900. In some embodiments, controller 710 to apply the alternating electric fields (e.g., TTFields) to a subject may be implemented with the apparatus 900. The apparatus 900 may include one or more processors 902, memory 903, one or more input devices (not shown), and one or more output devices 905.

In some embodiments, based on input 901, the one or more processors 902 may generate control signals to control the voltage generator to implement one or more embodiments described herein. As an example, input 901 is user input. As an example, input 901 may be from another computer in communication with the apparatus 900. The input 901 may be received in conjunction with one or more input devices (not shown) of the apparatus 900.

The memory 903 may be accessible by the one or more processors 902 (e.g., via a link 904) so that the one or more processors 902 can read information from and write information to the memory 903. The memory 903 may store instructions that, when executed by the one or more processors 902, implement one or more embodiments described herein. The memory 903 may be a non-transitory computer readable medium (or a non-transitory processor readable medium) containing a set of instructions thereon for processing a medical image of a subject to generate transducer layouts for application of TTFields to the subject, wherein when executed by a processor (such as one or more processors 902), the instructions cause the processor to perform one or more methods discussed herein, such as the methods 100, 200, and/or 300 of FIGS. 1-3 respectively.

The one or more output devices 405 may provide the status of the operation of the invention, such as transducer array selection, voltages being generated, and other operational information. The output device(s) 405 may provide visualization data according to some embodiments described herein.

The apparatus 900 may be an apparatus for processing a medical image of a subject to generate transducer layouts for application of TTFields to the subject, the apparatus including: one or more processors (such as one or more processors 902); and memory (such as memory 903) accessible by the one or more processors 902, the memory 903 storing instructions that when executed by the one or more processors 902, cause the apparatus 900 to perform one or more methods described herein, such as the methods 100, 200, and/or 300 of FIGS. 1-3, respectively.

ILLUSTRATIVE EMBODIMENTS

The invention includes other illustrative embodiments ("Embodiments") as follows.

Embodiment 1. A computer-implemented method for processing a medical image of a subject, the method comprising: presenting on a display a slice through the medical image of the subject, wherein the medical image comprises voxels; and performing automatic edge detection in the slice of the medical image to obtain a segmented slice, wherein the automatic edge detection is based on a user selected voxel in the slice of the medical image, wherein the automatic edge detection is based on a user controllable edge detection brush, wherein not all of the voxels selected by the edge detection brush are designated as an edge.

Embodiment 2. The method of embodiment 1, wherein performing automatic edge detection comprises: determining a radius of the edge detection brush for use in the automatic edge detection; and determining an edge threshold of the edge detection brush, wherein image values of voxels selected by the edge detection brush are designated as an edge based on the edge threshold.

Embodiment 3. The method of embodiment 1, wherein performing automatic edge detection comprises: determining the user selected voxel in the slice of the medical image; determining an edge detection image value based on the user selected voxel in the slice of the medical image; determining a size of the edge detection brush for use in the automatic edge detection; determining an edge threshold of the edge detection brush; determining a range of image values to designate as an edge based on the edge detection image value and the edge threshold; receiving user selected voxels in the slice based on the edge detection brush interacting with the voxels in the slice and based on the size of the edge detection brush; and designating user selected voxels in the slice as edge voxels in the slice based on the range of image values to designate as an edge.

Embodiment 4. The method of embodiment 3, wherein determining the edge detection image value based on the user selected voxel in the slice of the medical image comprises: determining a center image value as an image value of the user selected voxel in the slice of the medical image, wherein the user selected voxel is in a center of a user selected location; determining adjacent image values as image values of voxels adjacent to the user selected voxel; calculating an average image value based on the center image value and the adjacent image values; and assigning the edge detection image value as the average image value.

Embodiment 4A. The method of embodiment 4, wherein the voxels adjacent to the user selected voxel comprise eight voxels surrounding the user selected voxel.

Embodiment 5. The method of embodiment 3, wherein determining the edge detection image value based on the user selected voxel in the slice of the medical image comprises: determining a center image value as an image value of the user selected voxel in the slice of the medical image, wherein the user selected voxel is in a center of a user selected location; and assigning the edge detection image value as the center image value.

Embodiment 6. The method of embodiment 3, wherein the size of the edge detection brush is a radius of a circular edge detection brush.

Embodiment 7. The method of embodiment 3, wherein the user selection of the edge threshold for the edge detection brush comprises a percentage.

Embodiment 7A. The method of embodiment 3, wherein the user selection of the edge threshold for the edge detection brush comprises an image value.

Embodiment 8. The method of embodiment 3, wherein the range of image values to designate as an edge comprises a number M of image values in the range, an upper limit UL of the range, and a lower limit LL of the range, wherein the number M of image values in the range is: $M=N*(1-P)$, where a range of image values for the medical image has a maximum number N of image values, and where the user selection for the edge threshold is a percentage P, wherein the upper limit UL of the range is: $UL=IV+0.5*M$, where image value IV is the edge detection image value, and wherein a lower limit LL of the range is: $LL=IV-0.5*M$.

Embodiment 9. The method of embodiment 3, wherein the range of image values to designate as an edge comprises a number M of image values in the range, an upper limit UL of the range, and a lower limit LL of the range, wherein the number M of image values in the range is: $M=N*(1-(P*RL))$, where a range of image values for the medical image has a maximum number N of image values, where the user selection for the edge threshold is a percentage P, and where a range limiter is a percentage RL, wherein the upper limit UL of the range is: $UL=IV+0.5*M$, where image value IV is the edge detection image value, and wherein a lower limit LL of the range is: $LL=IV-0.5*M$.

Embodiment 10. The method of embodiment 3, wherein the edge threshold is an image value, wherein an upper limit of the range of image values is a sum of the edge detection image value and the edge threshold, and wherein a lower limit of the range of image values is a difference between the edge detection image value and the edge threshold.

Embodiment 11. The method of embodiment 3, wherein designating user selected voxels in the slice as edge voxels in the slice comprises: comparing image values of the user selected voxels to the range of image values.

Embodiment 12. The method of embodiment 3, wherein designating user selected voxels in the slice as edge voxels in the slice comprises, for each user selected voxel in the slice: designating the user selected voxel as an edge if an image value of the user selected voxel is in the range of image values; and designating the user selected voxel as not an edge if an image value of the user selected voxel is not in the range of image values.

Embodiment 12A. The method of embodiment 3, wherein an image value of a voxel of the slice comprises a whole number indicating an intensity of the voxel.

Embodiment 12B. The method of embodiment 3, wherein an image value of a voxel of the slice comprises a gray level value.

Embodiment 13. The method of embodiment 1, further comprising: performing automatic segmentation of a plurality of slices through the medical image to obtain automatically segmented slices through the medical image, the automatic segmentation based on the segmented slice.

Embodiment 14. The method of embodiment 13, wherein the automatically segmented slices are automatically segmented by interpolating between the segmented slice and a second segmented slice.

Embodiment 14A. The method of embodiment 13, wherein the automatically segmented slices through the medical image are situated between the segmented slice and a second segmented slice, wherein the automatically segmented slices are in a same direction as the segmented slice and the second segmented slice, wherein the automatically segmented slices are automatically segmented based on the segmented slice and the second segmented slice.

Embodiment 14B. The method of embodiment 14A, wherein a number of automatically segmented slices between the segmented slice and the second segmented slice is between 2 and 20.

Embodiment 14C. The method of embodiment 14A, wherein a number of automatically segmented slices between the segmented slice and the second segmented slice is between 2 and 5.

Embodiment 15. The method of embodiment 1, further comprising: generating a plurality of transducer layouts for application of tumor treating fields to the subject based on the segmented slice through the medical image.

Embodiment 16. The method of embodiment 1, wherein the segmented slice comprises at least one of a resection cavity or an edema of the subject having an edge detected by the automatic edge detection.

Embodiment 16A. The method of embodiment 1, wherein the medical image comprises a torso of the subject.

Embodiment 16B. The method of embodiment 1, wherein the medical image comprises a head of the subject.

Embodiment 16C. The method of embodiment 1, wherein the medical image comprises a computed tomography (CT) medical image, a magnetic resonance imaging (MRI) medical image, or a positron emission tomography (PET) medical image.

Embodiment 16D. A non-transitory processor readable medium containing a set of instructions thereon for processing a medical image of a subject, wherein when executed by a processor, the instructions cause the processor to perform a method comprising: presenting on a display a slice through the medical image of the subject, wherein the medical image comprises voxels; and performing automatic edge detection in the slice of the medical image to obtain a segmented slice, wherein the automatic edge detection is based on a user selected voxel in the slice of the medical image, wherein the automatic edge detection is based on a user controllable edge detection brush, wherein not all of the voxels selected by the edge detection brush are designated as an edge.

Embodiment 16E. An apparatus for processing a medical image of a subject, the apparatus comprising: one or more processors; and memory accessible by the one or more processors, the memory storing instructions that when executed by the one or more processors, cause the apparatus to perform a method comprising: presenting on a display a slice through the medical image of the subject, wherein the medical image comprises voxels; and performing automatic edge detection in the slice of the medical image to obtain a segmented slice, wherein the automatic edge detection is based on a user selected voxel in the slice of the medical image, wherein the automatic edge detection is based on a user controllable edge detection brush, wherein not all of the voxels selected by the edge detection brush are designated as an edge.

Embodiment 17. A computer-implemented method for processing a medical image of a subject, the method comprising: presenting on a display a first slice through a medical image of the subject, wherein the medical image comprises voxels; performing automatic edge detection in the first slice of the medical image to obtain a first segmented slice, wherein the edge detection is based on a user selected voxel in the first slice of the medical image; presenting on the display a second slice through the medical image of the subject, wherein the first slice and the second slice are in a same direction and are separated by a plurality of slices through the medical image; performing automatic edge detection in the second slice of the medical image to obtain a second segmented slice, wherein the edge detection is based on a user selected voxel in the second slice of the medical image; performing automatic segmentation of the plurality of slices between the first slice and the second slice based on the first segmented slice and the second segmented slice to obtain segmented slices, wherein a segmented medical image comprises the first segmented slice, the second segmented slice, and the segmented slices of the medical image.

Embodiment 17A. The method of embodiment 17, wherein the plurality of slices are automatically segmented by interpolating between the first slice and the second slice.

Embodiment 18. The method of embodiment 17, further comprising:

generating a plurality of transducer layouts for application of tumor treating fields to the subject based on the segmented medical image.

Embodiment 19. The method of embodiment 17, further comprising: defining a region of interest (ROI) in the medical image or in the segmented medical image for application of tumor treating fields to the subject; creating a three-dimensional model of the subject based on the segmented medical image, the three-dimensional model of the subject including the region of interest; generating a plurality of transducer layouts for application of tumor treating fields to the subject based on the three-dimensional model of the subject; selecting at least two of the transducer layouts as recommended transducer layouts; presenting the recommended transducer layouts; receiving a user selection of at least one recommended transducer layout; and providing a report for the at least one selected recommended transducer layout.

Embodiment 19A. A non-transitory processor readable medium containing a set of instructions thereon for processing a medical image of a subject, wherein when executed by a processor, the instructions cause the processor to perform a method comprising: presenting on a display a first slice through a medical image of the subject, wherein the medical image comprises voxels; performing automatic edge detection in the first slice of the medical image to obtain a first segmented slice, wherein the edge detection is based on a user selected voxel in the first slice of the medical image; presenting on the display a second slice through the medical image of the subject, wherein the first slice and the second slice are in a same direction and are separated by a plurality of slices through the medical image; performing automatic edge detection in the second slice of the medical image to obtain a second segmented slice, wherein the edge detection is based on a user selected voxel in the second slice of the medical image; performing automatic segmentation of the plurality of slices between the first slice and the second slice based on the first segmented slice and the second segmented slice to obtain segmented slices, wherein a segmented medical image comprises the first segmented slice, the second segmented slice, and the segmented slices of the medical image.

Embodiment 19B. An apparatus for processing a medical image of a subject, the apparatus comprising: one or more processors; and memory accessible by the one or more processors, the memory storing instructions that when executed by the one or more processors, cause the apparatus to perform a method comprising: presenting on a display a first slice through a medical image of the subject, wherein the medical image comprises voxels; performing automatic edge detection in the first slice of the medical image to obtain a first segmented slice, wherein the edge detection is based on a user selected voxel in the first slice of the medical image; presenting on the display a second slice through the medical image of the subject, wherein the first slice and the second slice are in a same direction and are separated by a plurality of slices through the medical image; performing automatic edge detection in the second slice of the medical image to obtain a second segmented slice, wherein the edge detection is based on a user selected voxel in the second slice of the medical image; performing automatic segmentation of the plurality of slices between the first slice and the second slice based on the first segmented slice and the second segmented slice to obtain segmented slices, wherein a segmented medical image comprises the first segmented slice, the second segmented slice, and the segmented slices of the medical image.

Embodiment 20. A computer-implemented method for processing a medical image of a subject, the method comprising: presenting on a display a slice through a medical image of the subject, wherein the medical image comprises voxels; performing automatic edge detection in the slice of the medical image using a user-controllable edge detection brush to obtain a segmented slice, wherein not all of the voxels selected by the edge detection brush are designated as an edge; performing automatic segmentation of a plurality of slices through the medical image to obtain automatically segmented slices through the medical image and a segmented medical image, the automatic segmentation based on the segmented slice; and generating a plurality of transducer layouts for application of tumor treating fields to the subject based on the segmented medical image.

Embodiment 20A. A non-transitory processor readable medium containing a set of instructions thereon for processing a medical image of a subject, wherein when executed by a processor, the instructions cause the processor to perform a method comprising: presenting on a display a slice through a medical image of the subject, wherein the medical image comprises voxels; performing automatic edge detection in the slice of the medical image using a user-controllable edge detection brush to obtain a segmented slice, wherein not all of the voxels selected by the edge detection brush are designated as an edge; performing automatic segmentation of a plurality of slices through the medical image to obtain automatically segmented slices through the medical image and a segmented medical image, the automatic segmentation based on the segmented slice; and generating a plurality of transducer layouts for application of tumor treating fields to the subject based on the segmented medical image.

Embodiment 20B. An apparatus for processing a medical image of a subject, the apparatus comprising: one or more processors; and memory accessible by the one or more processors, the memory storing instructions that when executed by the one or more processors, cause the apparatus to perform a method comprising: presenting on a display a slice through a medical image of the subject, wherein the medical image comprises voxels; performing automatic edge detection in the slice of the medical image using a user-controllable edge detection brush to obtain a segmented slice, wherein not all of the voxels selected by the edge detection brush are designated as an edge; performing automatic segmentation of a plurality of slices through the medical image to obtain automatically segmented slices through the medical image and a segmented medical image, the automatic segmentation based on the segmented slice; and generating a plurality of transducer layouts for application of tumor treating fields to the subject based on the segmented medical image.

Embodiment 20C. A computer-implemented method for processing a medical image of a subject, the method comprising: presenting on a display one or more user-selectable icons to display a slice through the medical image of the subject, wherein the medical image comprises voxels; and presenting on the display a user-selectable icon to perform automatic edge detection in the slice of the medical image to obtain a segmented slice, wherein the automatic edge detection is based on a user selected voxel in the slice of the medical image, wherein the automatic edge detection is based on a user-controllable edge detection brush, wherein not all of the voxels selected by the edge detection brush are designated as an edge.

Embodiment 20D. The method of embodiment 20C, further comprising: presenting on the display a user-selectable icon to determine a radius of the edge detection brush for use in the automatic edge detection; and presenting on the display a user-selectable icon to determine an edge threshold of the edge detection brush, wherein image values of voxels selected by the edge detection brush are designated as an edge based on the edge threshold.

Embodiment 20E. The method of embodiment 20C, further comprising: presenting on the display a user-selectable icon to perform automatic segmentation of a plurality of slices through the medical image to obtain automatically segmented slices through the medical image, the automatic segmentation based on the segmented slice.

Embodiment 20F. The method of embodiment 20C, further comprising: presenting on the display a user-selectable icon to generate a plurality of transducer layouts for application of tumor treating fields to the subject based on the automatically segmented slices through the medical image.

Embodiment 21. A method, machine, manufacture, and/or system substantially as shown and described.

Optionally, for each embodiment described herein, the voltage generation components supply the transducers with an electrical signal having an alternating current waveform at frequencies in a range from about 50 kHz to about 1 MHz and appropriate to deliver TTFields treatment to the subject's body.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention need not be limited to the described embodiments, but that it has the full scope defined by the language of the following claims, and equivalents thereof.

What is claimed is:

1. A computer-implemented method for processing a medical image of a subject, the method comprising:

presenting on a display a slice through the medical image of the subject, wherein the medical image comprises voxels; and performing automatic edge detection in the slice of the medical image to obtain a segmented slice, wherein the automatic edge detection is based on a user selected voxel in the slice of the medical image, wherein the automatic edge detection is based on a user controllable edge detection brush, wherein not all of the voxels selected by the edge detection brush are designated as an edge, wherein performing automatic edge detection comprises:

determining the user selected voxel in the slice of the medical image;

determining an edge detection image value based on the user selected voxel in the slice of the medical image;

determining a size of the edge detection brush for use in the automatic edge detection;

determining an edge threshold of the edge detection brush;

determining a range of image values to designate as an edge based on the edge detection image value and the edge threshold;

receiving user selected voxels in the slice based on the edge detection brush interacting with the voxels in the slice and based on the size of the edge detection brush; and designating user selected voxels in the slice as edge voxels in the slice based on the range of image values to designate as an edge, wherein determining the edge threshold of the edge detection brush comprises a user selection of the edge threshold, and wherein the user selection of the edge threshold for the edge detection brush comprises at least one of:

a percentage of pixels designated as edges, or an image value.

2. The method of claim 1, wherein performing automatic edge detection comprises:

determining a radius of the edge detection brush for use in the automatic edge detection.

3. The method of claim 1, wherein determining the edge detection image value based on the user selected voxel in the slice of the medical image comprises:

determining a center image value as an image value of the user selected voxel in the slice of the medical image, wherein the user selected voxel is in a center of a user selected location;

determining adjacent image values as image values of voxels adjacent to the user selected voxel;

calculating an average image value based on the center image value and the adjacent image values; and assigning the edge detection image value as the average image value.

4. The method of claim 1, wherein determining the edge detection image value based on the user selected voxel in the slice of the medical image comprises:

determining a center image value as an image value of the user selected voxel in the slice of the medical image, wherein the user selected voxel is in a center of a user selected location; and assigning the edge detection image value as the center image value.

5. The method of claim 1, wherein the size of the edge detection brush is a radius of a circular edge detection brush.

6. The method of claim 1, wherein the user selection of the edge threshold for the edge detection brush comprises at least the percentage of pixels designated as edges.

7. The method of claim 1, wherein the user selection of the edge threshold for the edge detection brush comprises at least the percentage of pixels designated as edges, wherein the range of image values to designate as an edge comprises a number M of image values in the range, an upper limit UL of the range, and a lower limit LL of the range, wherein the number M of image values in the range is:

$$M = N * (1 - P),$$

where a range of image values for the medical image has a maximum number N of image values, and where P represents the percentage of pixels designated as edges, wherein the upper limit UL of the range is:

$$UL = IV + 0.5 * M,$$

where image value IV is the edge detection image value, and wherein a lower limit LL of the range is:

$$LL = IV - 0.5 * M.$$

8. The method of claim 1, wherein the user selection of the edge threshold for the edge detection brush comprises at least the percentage of pixels designated as edges, wherein the number M of image values in the range is:

$$M = N * (1 - (P * RL)),$$

where a range of image values for the medical image has a maximum number N of image values, where P represents the percentage of pixels designated as edges, and where a range limiter is a percentage RL, wherein the upper limit UL of the range is:

$$UL = IV + 0.5 * M,$$

where image value IV is the edge detection image value, and wherein a lower limit LL of the range is:

$$LL = IV - 0.5 * M.$$

9. The method of claim 1, wherein the user selection of the edge threshold for the edge detection brush comprises at least the image value, wherein an upper limit of the range of image values is a sum of the edge detection image value and the edge threshold, and wherein a lower limit of the range of image values is a difference between the edge detection image value and the edge threshold.

10. The method of claim 1, wherein designating user selected voxels in the slice as edge voxels in the slice comprises:

comparing image values of the user selected voxels to the range of image values.

11. The method of claim 1, wherein designating user selected voxels in the slice as edge voxels in the slice comprises, for each user selected voxel in the slice:

designating the user selected voxel as an edge if an image value of the user selected voxel is in the range of image values; and designating the user selected voxel as not an edge if an image value of the user selected voxel is not in the range of image values.

12. The method of claim 1, further comprising:

performing automatic segmentation of a plurality of slices through the medical image to obtain automatically segmented slices through the medical image, the automatic segmentation based on the segmented slice.

13. The method of claim 12, wherein the automatically segmented slices are automatically segmented by interpolating between the segmented slice and a second segmented slice.

14. The method of claim 1, further comprising:

generating a plurality of transducer layouts for application of tumor treating fields to the subject based on the segmented slice through the medical image.

15. The method of claim 1, wherein the segmented slice comprises at least one of a resection cavity or an edema of the subject having an edge detected by the automatic edge detection.

16. A computer-implemented method for processing a medical image of a subject, the method comprising:

presenting on a display a first slice through a medical image of the subject, wherein the medical image comprises voxels;

performing automatic edge detection in the first slice of the medical image to obtain a first segmented slice, wherein the automatic edge detection is based on a user selected voxel in the first slice of the medical image;

presenting on the display a second slice through the medical image of the subject, wherein the first slice and the second slice are in a same direction and are separated by a plurality of slices through the medical image;

performing automatic edge detection in the second slice of the medical image to obtain a second segmented slice, wherein the automatic edge detection is based on a user selected voxel in the second slice of the medical image;

performing automatic segmentation of the plurality of slices between the first slice and the second slice based on the first segmented slice and the second segmented slice to obtain segmented slices, wherein a segmented medical image comprises the first segmented slice, the second segmented slice, and the segmented slices of the medical image, wherein performing automatic edge detection in the first slice comprises:

determining the user selected voxel in the first slice of the medical image;

determining an edge detection image value based on the user selected voxel in the first slice of the medical image;

determining a size of the edge detection brush for use in the automatic edge detection;

determining an edge threshold of the edge detection brush;

determining a range of image values to designate as an edge based on the edge detection image value and the edge threshold;

receiving user selected voxels in the first slice based on the edge detection brush interacting with the voxels in the first slice and based on the size of the edge detection brush; and designating user selected voxels in the first slice as edge voxels in the first slice based on the range of image values to designate as an edge, wherein determining the edge threshold of the edge detection brush comprises a user selection of the edge threshold, and wherein the user selection of the edge threshold for the edge detection brush comprises at least one of:

a percentage of pixels designated as edges, or an image value.

17. The method of claim 16, further comprising:

generating a plurality of transducer layouts for application of tumor treating fields to the subject based on the segmented medical image.

18. The method of claim 16, further comprising:

defining a region of interest (ROI) in the medical image or in the segmented medical image for application of tumor treating fields to the subject;

creating a three-dimensional model of the subject based on the segmented medical image, the three-dimensional model of the subject including the region of interest;

generating a plurality of transducer layouts for application of tumor treating fields to the subject based on the three-dimensional model of the subject;

selecting at least two of the transducer layouts as recommended transducer layouts;

presenting the recommended transducer layouts;

receiving a user selection of at least one recommended transducer layout; and providing a report for the at least one selected recommended transducer layout.

19. A computer-implemented method for processing a medical image of a subject, the method comprising:

presenting on a display a slice through a medical image of the subject, wherein the medical image comprises voxels;

performing automatic edge detection in the slice of the medical image using a user-controllable edge detection brush to obtain a segmented slice, wherein not all of the voxels selected by the edge detection brush are designated as an edge;

performing automatic segmentation of a plurality of slices through the medical image to obtain automatically segmented slices through the medical image and a segmented medical image, the automatic segmentation based on the segmented slice; and generating a plurality of transducer layouts for application of tumor treating fields to the subject based on the segmented medical image, wherein performing automatic edge detection comprises:

determining a user selected voxel in the slice of the medical image;

determining an edge detection image value based on the user selected voxel in the slice of the medical image;

determining a size of the edge detection brush for use in the automatic edge detection;

determining an edge threshold of the edge detection brush;

determining a range of image values to designate as an edge based on the edge detection image value and the edge threshold;

receiving user selected voxels in the slice based on the edge detection brush interacting with the voxels in the slice and based on the size of the edge detection brush; and designating user selected voxels in the slice as edge voxels in the slice based on the range of image values to designate as an edge, wherein determining the edge threshold of the edge detection brush comprises a user selection of the edge threshold, and wherein the user selection of the edge threshold for the edge detection brush comprises at least one of:

a percentage of pixels designated as edges, or an image value.

* * * * *